(12) United States Patent
Boessmann

(10) Patent No.: US 7,952,625 B2
(45) Date of Patent: May 31, 2011

(54) CALIBRATION ELEMENT FOR CALIBRATING THE MAGNIFICATION RATIO OF A CAMERA, AND A CALIBRATION METHOD

(75) Inventor: Hartmut Boessmann, Steinhagen (DE)

(73) Assignee: Texmag GmbH Vertriebsgesellschaft, Thalwil (CH)

( * ) Notice: Subject to any disclaimer, the term of this patent is extended or adjusted under 35 U.S.C. 154(b) by 380 days.

(21) Appl. No.: 12/321,413

(22) Filed: Jan. 21, 2009

(65) Prior Publication Data

US 2009/0185038 A1 Jul. 23, 2009

(30) Foreign Application Priority Data

Jan. 21, 2008 (EP) ..................................... 08001043
Jan. 25, 2008 (EP) ..................................... 08001442

(51) Int. Cl.
*H04N 17/00* (2006.01)
*H04N 7/18* (2006.01)
(52) U.S. Cl. .......................... 348/287; 348/136; 348/137
(58) Field of Classification Search .................. 348/135, 348/136, 137, 140, 141, 142, 144, 145, 175, 348/176, 180, 187, 188, 189
See application file for complete search history.

(56) References Cited

U.S. PATENT DOCUMENTS

| 5,149,965 | A  | * | 9/1992  | Marks ........................ 250/252.1 |
| 6,459,772 | B1 | * | 10/2002 | Wiedenhoefer et al. ....... 378/163 |
| 6,611,292 | B1 | * | 8/2003  | Tsai et al. ..................... 348/345 |
| 6,915,072 | B2 | * | 7/2005  | Takahashi et al. ............ 396/296 |

FOREIGN PATENT DOCUMENTS

EP 1 251 347 A1 10/2002

* cited by examiner

*Primary Examiner* — Tuan Ho
*Assistant Examiner* — Peter Chon
(74) *Attorney, Agent, or Firm* — Robert L. Epstein; Epstein Drangel LLP

(57) ABSTRACT

A calibration element (1) serves for calibrating the magnification ratio of a camera (3). The calibration element (1) has at least one calibration region (4) in which at least one perforation (5) or indentation is provided. The perforation (5) or indentation can be detected by the camera. The calibration element (1) is sufficiently slight in the calibration region (4) that the detection of an upper edge or lower edge of the perforation (5) or indentation produces only negligible differences. In order to determine the dependence of the magnification ratio on the thickness, the calibration element (1) additionally has at least one support foot (8), whose length (9) is selected in such a way as thereby to produce a variation in the measured magnification ratio of the camera image that can be evaluated.

11 Claims, 4 Drawing Sheets

Figure 1:
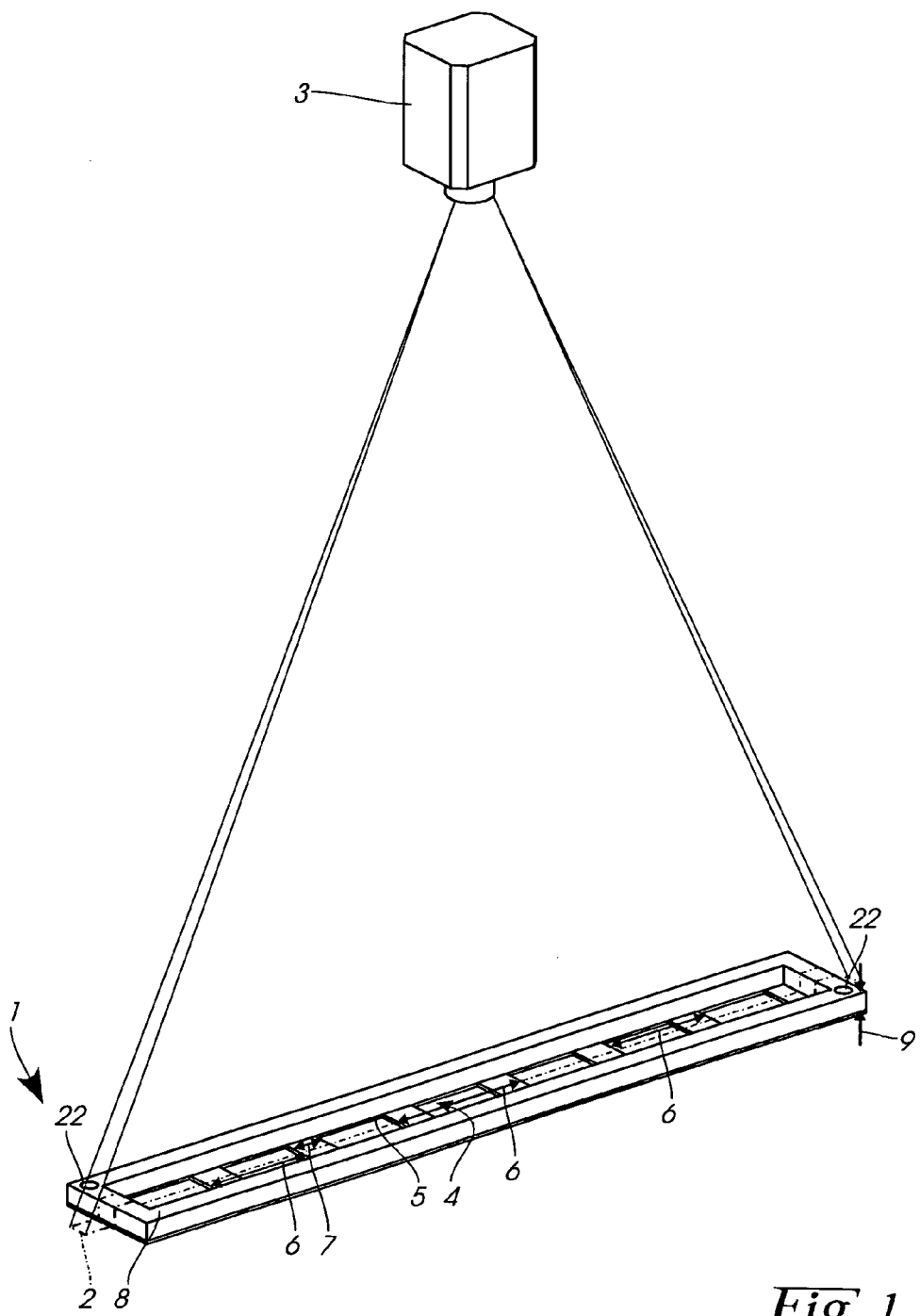

CALIBRATION ELEMENT FOR CALIBRATING THE MAGNIFICATION RATIO OF A CAMERA, AND A CALIBRATION METHOD

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The invention relates to a calibration element for calibrating the magnification ratio of a camera, and a calibration method 2. Description of Prior Art Including Information Disclosed Under 37 CFR 1.97 and 1.98

There is known from DE 101 18 886 B4 a calibration ruler that includes a printed marking that can be detected by a camera. This marking codes the respective location such that it is also possible to determine the exact length of the detection range of the camera. This calibration ruler assumes, however, that the object to be detected is flat and is located in a defined and invariable position. In the case of product webs in the fields of textiles, papers and plastics, this condition can be fulfilled without any problem because of the negligible product web thickness, but in the case of rubber webs, however, this restriction leads to intolerable problems. It is necessary here also to take account of the influence of the web thickness on the calibration of the camera.

BRIEF SUMMERY OF THE INVENTION

It is the object of the invention to provide a calibration element of the type mentioned at the beginning that also takes account of the dependence of an object to be detected on thickness in conjunction with a simple design. It is also intended to provide a corresponding calibration method.

This object is achieved according to the invention with a calibration element serving for calibrating the magnification ratio of a camera. It is preferred to make use as camera of a CCD or CMOS camera, it also being possible as an alternative to use other imaging methods. Again, whether the camera is a matrix or line camera plays no role. In particular, in cases of application where the aim is to utilize the camera to scan objects in the form of running product webs, a line camera that is aligned transverse to the running direction is completely sufficient. A calibration in the line direction is sufficient in this case. In the case of a matrix camera, the calibration can be performed in row and/or column direction depending on application. The magnification ratio of the camera is important for determining exact measured variables. However, it is dependent both on the position and on the alignment of the camera. Moreover, the magnification ratio also changes with the thickness of the object to be examined, since the surface viewed by the camera lies closer to the camera for relatively thick objects than for relatively thin objects. These differences play a role, in particular, when objects are detected exactly using measurement technology. This problem is solved by using a calibration element that has at least one calibration region. Located in this calibration region is at least one perforation or indentation that can be detected by the camera. The size or the mutual spacing of the perforation and indentation is known in this case, and so the measured variables detected by the camera can be compared with known geometric dimensions of the calibration element. It is possible in this way to determine the magnification ratio of the camera, which is dependent on the mounting and alignment. If a number of perforations and indentations are provided, this magnification ratio can also be calculated as a function of the location in the field of view of the camera, in order in this way also to correct imaging errors of the objective such as, for example, a trapezoidal distortion of the camera image.

In order to additionally determine the dependence of the magnification ratio on the thickness of the object to be detected, it is fundamentally sufficient to calibrate the camera in two different object planes if the positions of these planes are known. It is not expedient in this case to use a calibration element with a thick calibration region, since this gives rise to the problem of an unreliable detection of the upper and lower edges of the calibration element. In order to achieve this object, the calibration element has at least one support foot whose length is selected in such a way that a variation which can be evaluated is produced in the magnification ratio of the camera image by rotating the calibration element and setting it down on the at least one support foot. The at least one support foot is at least twice as long as the thickness of the calibration element in the calibration region. Consequently, given a rotated position of the calibration element the calibration region is located in a measurable fashion at the camera, and so the magnification ratio varies correspondingly. This measurable variation in the magnification ratio then produces the desired thickness dependence of the object, and so the magnification ratio of the camera image is calibrated in this way as a function of the respective object thickness. Fundamentally, it is also intended to determine the magnification ratio as a function of the location in the field of view of the camera, in order to be able to use the camera to execute geometric measurements that are as accurate as possible.

When detecting the calibration element of the camera, the fundamental problem arises that the camera detects the upper edge, on the one hand, and the lower edge, on the other hand, of the calibration element, the lower edge sometimes being covered by the upper edge and depending on the position of the camera. In order to avoid calibration errors because of these unknowns, in the calibration region the calibration element has such a slight wall thickness that upper and lower edges of the perforations and/or indentations produce differences in the camera image that are negligible for the calibration procedure. Because of this thin wall thickness of the calibration element in the calibration region, the camera substantially sees only one edge in the region of the perforation, and so faults in the detection of the perforation and/or indentation are excluded.

It is advantageous, when the calibration element having a thickness of at most 2 mm in the calibration region. In the case of the dimensions and alignments of the camera that occur in practice, the upper edge and lower edge of the calibration element can in this case no longer be distinguished and so a measurement error associated therewith lies in the range of a pixel resolution of the camera, and can therefore be neglected.

A length of at least 10 mm has proved successful for the support foot. Particularly in the case of industrial applications with camera distances in the range of at most one meter, a sufficiently accurate measurable variation in the magnification ratio already results in this way, and so the dependence of the magnification ratio on the object thickness is sufficiently accurately calibrated in this way.

If only a single support foot is used, this is preferably provided in the middle of the calibration element in order to keep the latter in equilibrium when standing on the support foot. Alternatively, it is also possible to provide a number of support feet, and/or to design the at least one support foot as a web projecting from the calibration element. It is advantageous in this case when the at least one support foot is provided at the edge of the calibration element. In this way, the at least one support foot protects the calibration region of the calibration element against the effects of force, and thus against destruction. This is important particularly in the harsh industrial sector.

A particularly effective protection of the calibration region results from a U-shaped or frame-shaped design of the support foot. Moreover, in this case the support foot leads to increased mechanical strength of the calibration element and, in particular strengthens the sensitive calibration region. This also thereby increases the dimensional stability of the calibration region.

In order to avoid uncertainty in the detection of, on the one hand, an upper edge and, on the other hand, of a lower edge of the calibration element, it is advantageous when the calibration element has at least one indexing means. This indexing means can be designed, for example, as a hole, depression, pin or the like, and corresponds to an appropriate indexing means in the detection region of the camera. It is ensured in this way that the calibration element is always arranged in an identical, reproducible way. It is thereby clear which structures of the calibration element are detected at the upper edge, and which at the lower edge of the camera. A particularly thin design of the calibration element in the calibration region is not required in this case.

The calibration method in accordance the invention has proved successful for calibrating the camera. In this case, at least one calibration element of the aforedescribed type is laid in a field of view of the camera and the first image is produced. This image then includes geometric data of the calibration element together with imaging functions of the camera that are still fundamentally unknown. These imaging functions depend, in particular, on the position and alignment of a camera, and on the focal length and setting of the camera objective. Once the geometric properties of the calibration element are known, the magnification ratio of the camera can be calculated by comparing the camera image with the geometric variables of the calibration element. In order, in addition, to take account of the dependence of the magnification ratio on the object thickness, the calibration element is rotated and a further image is produced using the camera. Here, there is no change in the geometric properties of the calibration element itself. All that happens is that the calibration region is moved closer to the camera by the length of the at least one support foot. Subsequently, a linear function of the magnification ratio of the object thickness is calculated from the variation in the magnification ratio that is associated therewith. Here, the magnification ratio corresponds in the case of the first image produced to the object thickness zero and an object thickness that corresponds to the length of the support foot in the case of the second image produced. Consequently, the magnification ratio can be calculated for each desired object thickness by applying this linear function.

It is advantageous when the magnification ratio is calculated as a function of the location. This can be brought about, in particular, by the calibration element having a number of perforations or indentations such that in this way a plurality of geometric properties are present in the field of view of the camera. These various geometric properties can in this case enable an exact calibration even of distorted images. It is fundamentally adequate in this case to determine the dependence of the thickness of the magnification ratio as a function of location, since the functions of the magnification ratio are essentially decoupled from the thickness, on the one hand, and from the location, on the other hand.

In order for the optical detection of the calibration element by the camera to be configured as precisely as possible, it is when edges to be evaluated in the images of the camera are only those in the case of which end faces of the calibration element are invisible to the camera. The visibility of the end faces of the calibration element depends exclusively on the relative position between the respective end face, on the one hand, and the camera, on the other hand. If—seen perpendicular to the calibration element—the perforation or indentation is located to the left of the camera, for example, only the left-hand end faces of the perforation or indentation can be seen by the camera. In this case, only the right-hand end faces in the camera image are evaluated. If the perforation or indentation is, by contrast, located to the right of the camera, the left-hand edges of the perforation or indentation are evaluated. If, by contrast, the perforation is positioned both to the left and to the right of the camera, it is impossible to evaluate either of the two end faces properly. In this case, the nearest edges of the respectively neighboring perforations and/or indentations are used. It is ensured in this way that an erroneous evaluation of the lower edge of the calibration element averted from the camera is excluded.

BRIEF DESCRIPTION OF THE SEVERAL VIEWS OF DRAWINGS

Figure 2:
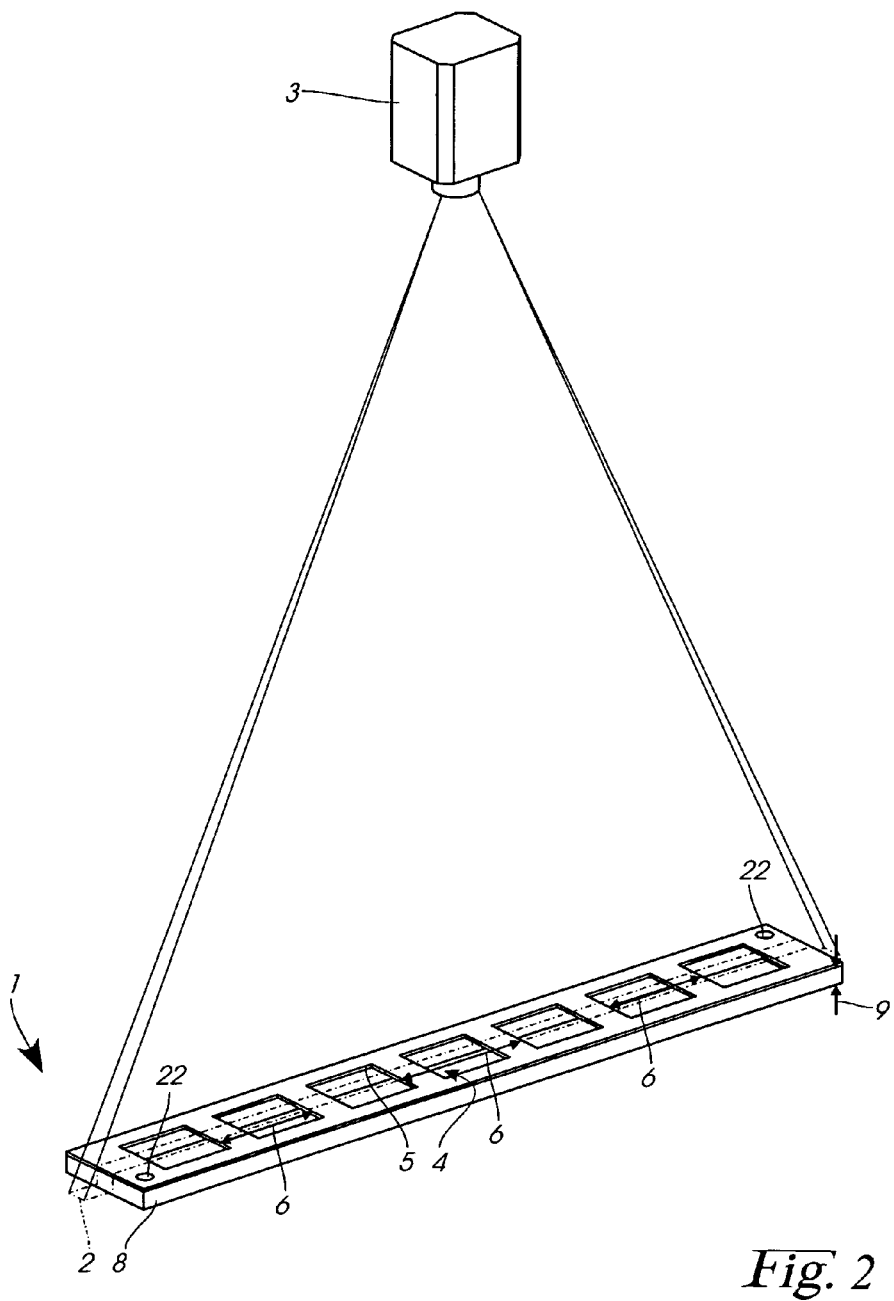
Figures 3, 4:
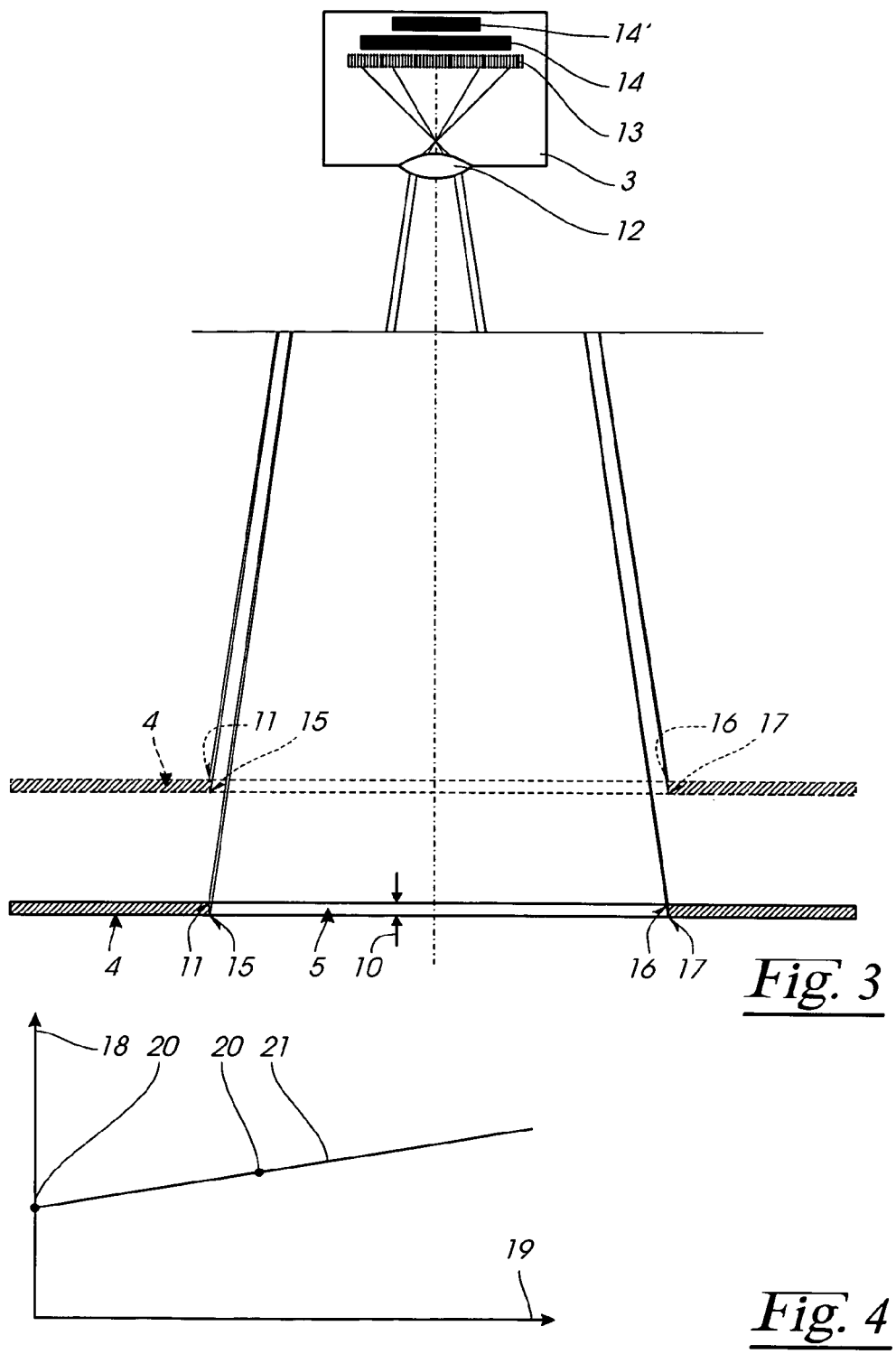
Figure 5:
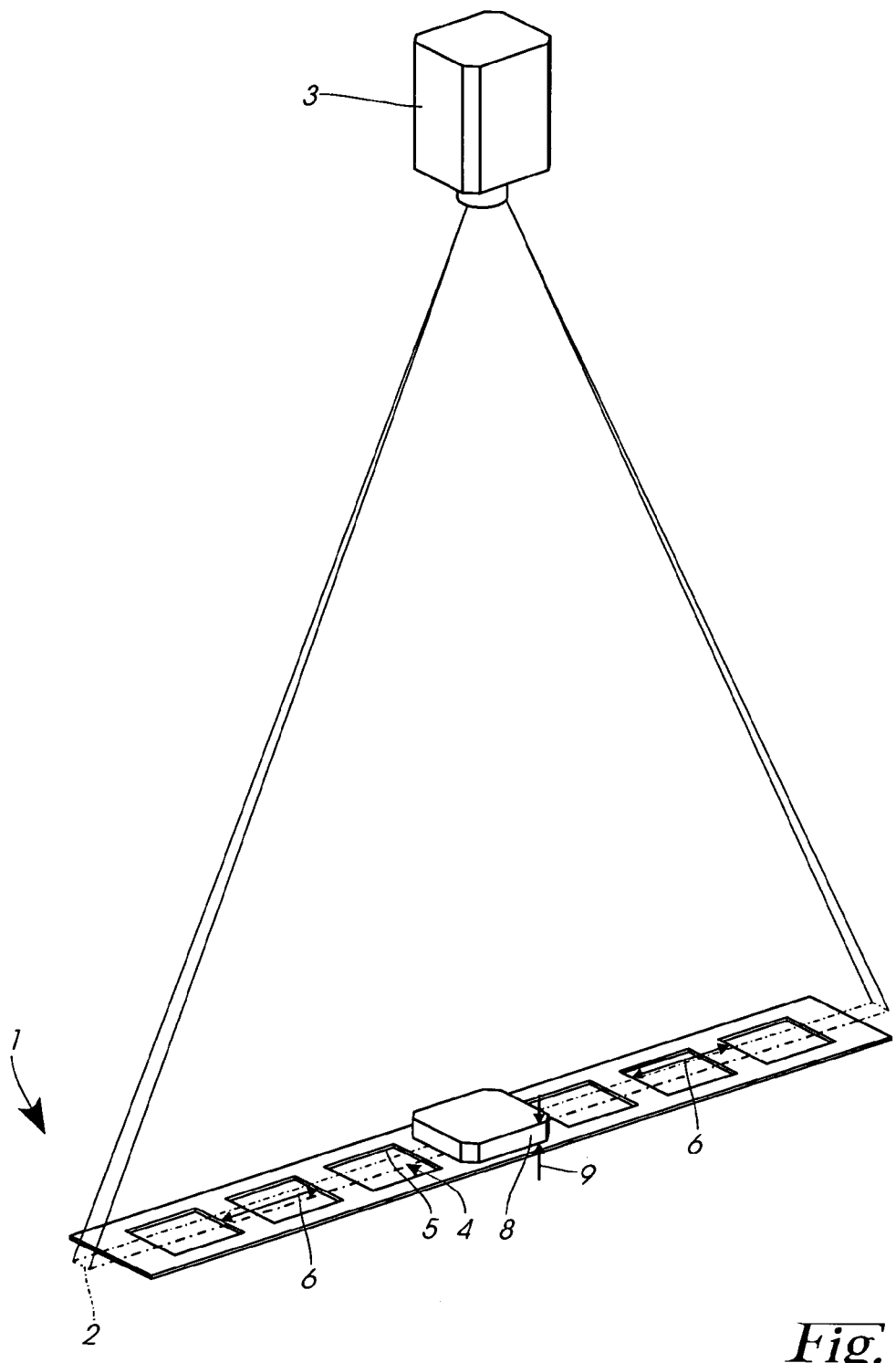

To these and to such other objects that may hereinafter appears, the present invention relates to a heating apparatus as described in detail in the following specification and recited in the annexed claims, taken together with the accompanying drawing in which shows:

FIG. 1: a two dimensional illustration of a calibration element with a camera, FIG. 2: the illustration in accordance with FIG. 1 with a rotated calibration element, FIG. 3: an enlarged illustration of a detail of the arrangement in accordance with FIG. 1, FIG. 4: a diagram, and FIG. 5: an alternative embodiment of the calibration element.

DETAILED DESCRIPTION OF THE INVENTION

The calibration element 1 in accordance with FIG. 1, which preferably consists of an iron material, is provided in a field of view 2 of a camera 3. The camera 3 is designed in this case as a line camera such that the field of view 2 forms a long, but at the same time narrow, rectangle.

The calibration element 1 has a central calibration region 4 in which a number of perforations 5 are provided. The camera 3 is able to detect these perforations 5 with rich contrast. The limiting edges of the perforations 5 have known calibration lengths. With the aid an image recorded by the camera 3, the magnification ratio of the camera 3 over the field of view 2, can be calculated from the known calibration lengths 6 and distances 7. When a real object is recorded with the aid of the camera 3, it is possible on the basis of this calculation to calculate the exact dimension of the object in the field of view 2 of the camera 3.

The calibration element 1 also has a support foot 8 that extends in the shape of a frame around the calibration region 4. This support foot 8 lends an advantageous dimensional rigidity to the calibration element 1 such that the calibration region 4 can be designed with a relatively thin wall thickness. In the exemplary embodiment, the calibration region 4 and the support foot 8 are separately provided parts that are subsequently interconnected. Alternatively, the calibration element can also be fabricated in one piece.

In the region of the support foot 8, the calibration element 1 has two indexing means 22 that are designed purely by way of example in the form of bores in the exemplary embodiment in accordance with FIG. 1.

Alternatively, it is also possible to make use of any desired other indexing means such as, for example, pins. Indexing means 22 ensures a reproducible, exact positioning of the calibration element 1 relative to the camera 3, and this facilitates the detection of the perforations 5.

FIG. 2 shows the arrangement in accordance with FIG. 1, the calibration element 1 having been rotated. The calibration element 1 thereby rests on the support foot 8. In this arrangement the calibration region 4 of the calibration element 1 comes closer to the camera 3 by a height 9 of the support foot 8. This affects the magnification ratio of the camera 3 such that it is possible in this way to determine a dependence of the magnification ratio on an object thickness.

FIG. 3 shows an enlarged, sectional illustration of a detail of the arrangement in accordance with FIGS. 1 and 2, with a cut beam path. It is to be seen, in particular, from this illustration that the calibration element 1 has a relatively slight wall thickness 10 in the calibration region 4. An upper edge 11 of the perforation 5 supplies a first image 14 on a photo detector 13 by means of an objective 12 of the camera 3. A lower edge 15 of the same perforation 5 is so close in this case to the upper edge 11 that it supplies the same first image 14 as the upper edge 11 in the case of the present magnification ratios. Consequently, differences resulting from the detection of the upper edge 11, on the one hand, and of the lower edge 15, on the other hand, of the perforation 5 cause errors of at most one pixel, that is to say of the accuracy of the photo detector 13. If the resolution of the photo detector 13 does not need to be completely utilized for the respective application, it is also possible to tolerate slightly different images 14 on the upper edge 11 and lower edge 15. Corresponding geometric conditions result in the case of the right hand upper edge 16 and lower edge 17.

With the rotated calibration element 1, the calibration region 4 lies closer to the camera 3, and this is illustrated in FIG. 3 by dashed lines. The upper edge 11 and lower edge 15 in this case supply a second image 14' on the photo detector 13 that is sufficiently widely spaced from the first image 14. What is important here is not the actual position of the first image 14 and second image 14' on the photo detector 13, but only the width of the perforation 5 in the camera image. In order to obtain a high accuracy, it is preferred to measure the distances of perforations 5 lying as far apart as possible. Furthermore, it is preferred to evaluate those upper edges 11, 16 for which the corresponding lower edges 15, 17 are not located in the field of view of the camera 3.

Given known dimensions of the calibration element 1, the first image 14 and second image 14' are used to determine magnification ratios 18 as a function of the object thickness 19 of the object to be examined. The first image 14 corresponds in this case to a thickness zero, while the second image 14' corresponds to the height 9. Two points 20 that define a linear function 21 are obtained in this way in the diagram in accordance with FIG. 4. This linear function 21 yields the corresponding magnification ratio 18 for each object thickness 19 such that the camera 3 is calibrated for any desired object thicknesses.

FIG. 5 shows an alternative embodiment of the calibration element 1 in accordance with FIG. 1. In this embodiment, the support foot 8 is designed as a central block around which the calibration region 4 extends.

Since some exemplary embodiments of the present invention are not shown or described, it must be understood that a multiplicity of changes and modifications of this exemplary embodiment described are possible, without departing from the essential idea and scope of protection of the invention defined by the claims.

LIST OF REFERENCE NUMERALS

1 Calibration element
2 Field of view
3 Camera
4 Calibration region
5 Perforation
6 Calibration length
8 Support foot
9 Height
10 Wall thickness
11 Upper edge
12 Objective
13 Photo detector
14 First image
14' Second image
15 Lower edge
16 Upper edge
17 Lower edge
18 Magnification ratio
19 Object thickness
20 Point
21 Linear function
22 Indexing means

The invention claimed is:

1. A calibration element for a camera being able to be directed to an object, having a thickness, said camera producing at least one image and having magnification ratios, being dependent on said object thickness said calibration element calibrating said magnification ratio of said camera, said calibration element having at least one calibration region, having a wall thickness therein, said calibration element is provided with at least one of a perforation or indentation in said calibration region which is detected by said camera, wherein in order to determine said magnification ratio dependence on said object thickness said calibration element having at least one support foot having a length, said length of said support foot is selected in such a way that by rotating said calibration element and setting it down on the at least one support foot a variation in said magnification ratio can be evaluated from said camera image, said length of said at least one support foot being at least twice as large as said wall thickness of said calibration element in said calibration region.

2. The calibration element as claimed in claim 1, wherein said calibration element in said calibration region having upper edges and lower edges and said calibration element having said wall thickness so slight that said upper and said lower edges producing differences in said camera image that are negligible for calibration.

3. The calibration element as claimed in claim 2, wherein said wall thickness being at most 2 mm in said calibration region.

4. The calibration element as claimed in claim 1, wherein said at least one support foot being at least 10 mm long.

5. The calibration element as claimed in claim 1, wherein said calibration element having an edge and said at least one support foot is provided at said edge of said calibration element.

6. The calibration element as claimed in claim 1, wherein said at least one support foot extends in the shape of a U around said calibration element.

7. The calibration element as claimed in claim 1, wherein said at least one support foot extends in the shape of a frame around said calibration element.

8. The calibration element as claimed in claim 1, wherein said calibration element having at least one indexing means for securing position of said calibration element.

9. A calibration method for a camera, having a field of view, said camera being directed to at least one calibration element having known dimensions during a calibration process and said camera being directed to an object, having a thickness, during a measuring process, said camera producing at least one object image of said object during said measuring process, and having a magnification ratio, being dependend on said object thickness said calibration element having at least one calibration region, having a wall thickness therein, said calibration element is provided with at least one of perforation and indentation in said calibration region being detected by said camera, wherein during said calibration process said calibration element being laid in said field of view of said camera and a first image being produced by said camera with a first magnification ratio, wherein said calibration element being subsequently rotated and a second image being produced by said camera with a second magnification ratio, there being calculated from said first and second image in conjunction with said known dimensions of said calibration element said first and said second magnification ratio, defining two points of a linear function of said magnification ratio of an object thickness, at least one individual magnification ratio being calculated from said linear function calculating said object thickness.

10. The calibration method as claimed in claim 9, wherein said magnification ratio is calculated as a function of the location.

11. The calibration method as claimed in claim 9, wherein said calibration element having end faces, said first and second image of said camera containing edges being evaluated corresponding to said end faces of said calibration element said end faces being invisible to said camera.

* * * * *